Patent Number: 4,840,880
Date of Patent: Jun. 20, 1989

COLOR PHOTOGRAPHIC RECORDING MATERIAL CONTAINING A YELLOW DIR COUPLER

[75] Inventors: Hans Öhlschläger; Günter Renner, both of Bergisch Gladbach; Friedrich-Wilhelm Kunitz; Heinrich Odenwälder, both of Leverkusen; Dirk Hübner, Cologne, all of Fed. Rep. of Germany

[73] Assignee: Agfa-Gevaert Aktiengesellschaft, Leverkusen, Fed. Rep. of Germany

[21] Appl. No.: 75,574

[22] Filed: Jul. 20, 1987

[30] Foreign Application Priority Data

Aug. 2, 1986 [DE] Fed. Rep. of Germany ....... 3626219

[51] Int. Cl.⁴ .............................................. G03C 7/36
[52] U.S. Cl. ..................... 430/505; 430/506; 430/544; 430/557
[58] Field of Search ................ 430/505, 544, 557, 389

[56] References Cited

U.S. PATENT DOCUMENTS

| | | | |
|---|---|---|---|
| 4,201,584 | 5/1980 | Monbaliu et al. | 430/389 |
| 4,273,861 | 6/1981 | Shiba et al. | 430/544 |
| 4,326,024 | 4/1982 | Kobayashi et al. | 430/557 |
| 4,359,521 | 11/1982 | Fryberg et al. | 430/557 |
| 4,368,255 | 1/1983 | Borg | 430/544 |
| 4,579,816 | 4/1986 | Öhlschläger et al. | 430/544 |

Primary Examiner—Paul R. Michl
Assistant Examiner—Mark R. Buscher
Attorney, Agent, or Firm—Connolly & Hutz

[57] ABSTRACT

High interimage effects and edge effects can be obtained in multilayer color photographic recording materials if yellow DIR couplers of formula I are used therein, particularly if used in green sensitized or red sensitized layers. Sharpness and color reproduction are substantially improved.

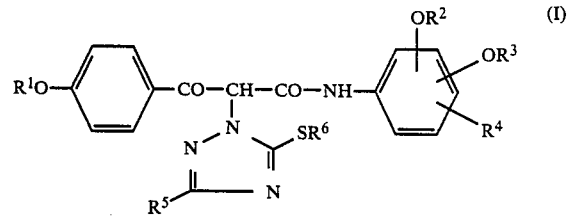

wherein
$R^1$ denotes a straight chained or branched alkyl group with up to 18 carbon atoms;
$R^2$, $R^3$ denote identical or different alkyl groups with up to 18 carbon atoms;
$R^4$ denotes H, halogen, alkyl with up to 6 carbon atoms or alkoxy with up to 6 carbon atoms;
$R^5$ denotes H or alkyl with up to 9 carbon atoms; and
$R^6$ denotes a saturated or unsaturated aliphatic group with up to 10 carbon atoms, the total number of carbon atoms in $R^5$ and $R^6$ being not less than 5 and not greater than 10.

2 Claims, No Drawings

COLOR PHOTOGRAPHIC RECORDING MATERIAL CONTAINING A YELLOW DIR COUPLER

This invention relates to a colour photographic recording material having at least one light sensitive silver halide emulsion layer containing a yellow coupler which releases a development inhibitor in the process of colour development.

It is known to carry out chromogenic development in the presence of compounds from which diffusible substances capable of inhibiting the development of silver halide are released in imagewise distribution in the process of development. Compounds of this kind are known as so called DIR compounds (DIR=development inhibitor releasing) These DIR compounds may be of the kind which react with the oxidation product of a colour developer to release an inhibitor and at the same time form a dye (DIR couplers) or they may be compounds which release the inhibitor without forming a dye. The latter compounds are referred to as DIR compounds in the narrower sense of the word.

DIR couplers have been disclosed, for example, in U.S. Pat. Nos. 3,148,062, 3,227,554, 3,615,506 and 3,617,291.

The released development inhibitors are generally heterocyclic mercapto compounds or derivatives of benzotriazole. DIR compounds which mainly give rise to colourless products in the coupling reaction are mentioned, for example, in U.S. Pat. No. 3,632,345, DE-A No. 23 59 295 and De-A No. -25 40 959. DIR compounds may be used to produce numerous photographic effects which influence the quality of the image. These effects include, for example, lowering of the gradation, formation of a finer coloured grain, improvement in the sharpness of the image by the so called edge effect and improvement in the colour purity and brilliance by so called inter image effects. See, for example, the publication entitled "Development Inhibitor Releasing (DIR) Couplers in Colour Photography" by C. R. Barr, J. R. Thirtle and P. W. Vittum in Photographic Science and Engineering 13, 74 (1969).

The DIR compounds which couple to form colourless products have the advantage over DIR couplers which give rise to coloured products in that they are universally applicable so that one and the same compound may be used in all the light sensitive layers of a colour photographic recording material, regardless of the colour to be produced. DIR couplers on the other hand, owing to the colour produced from them, can only be used in some of the light sensitive layers if the colour side densities to which they give rise are not acceptable in the other layers. Set against this advantage of DIR compounds is the disadvantage that they are generally less reactive than DIR couplers. On the whole, therefore, only DIR couplers have been used in the past, and if necessary two or more different couplers were used in the same photographic material so that the layers sensitized to different regions of the spectrum could be associated with different DIR couplers according to the colour produced from the latter.

DIR couplers derived from yellow couplers and containing a 3-alkylthio-1,2,4-triazolyl group as releasable inhibitor are described in DE-A No. 128 42 063. When the DIR couplers described in the said specification are used in a blue sensitive silver halide emulsion layer, the colour gradation in this layer may be considerably reduced but the effect on adjacent silver halide layers, in particular on adjacent green sensitive and/or red sensitive silver halide emulsion layers is comparatively slight. Only weak inter image effects can therefore be obtained with the known DIR couplers. DIR couplers also derived from yellow couplers and containing a releasable 3-alkylthio-5-furyl-1,2,4-triazole group are described in DE-A- No. 34 27 235. These couplers have a satisfactory remote effect in the sense of an inter image effect when used in the blue sensitive layer. They may also be used successfully in green sensitive layers but are then required at higher concentrations to produce an adequate inter image effect, with the result that the yellow side density which must be compensated is too high. These compounds are virtually ineffective in red sensitive layers.

It is an object of the present invention to provide a colour photographic recording material containing yellow DIR couplers with which comparatively high inter image effects can be produced even when they are used in magenta or cyan layers.

The present invention relates to a colour photographic recording material having at least one light sensitive silver halide emulsion layer and a DIR coupler associated with this layer, this coupler being a yellow coupler having a releasable 1,2,4-triazolyl group attached in the coupling position, characterised in that the DIR coupler corresponds to the following formula I

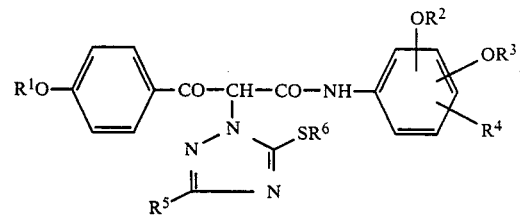

wherein
$R^1$ denotes a straight chained or branched alkyl group with up to 18 carbon atoms;
$R^2$ and $R^3$ denote identical or different alkyl groups with up to 18 carbon atoms;
$R^4$ denotes H, halogen, alkyl with up to 6 carbon atoms or alkoxy with up to 6 carbon atoms;
$R^5$ denotes H or alkyl with up to 9 carbon atoms and
$R^6$ denotes a saturated or unsaturated aliphatic group with up to 10 carbon atoms,
and the total number of carbon atoms in $R^5$ and $R^6$ is not less than 5 and not greater than 10.

An alkyl group denoted by $R^1$ in formula I may be, for example, a methyl, ethyl, propyl, isopropyl, n-butyl, dodecyl or hexadecyl group. It may be substituted, for example it may be an alkoxyalkyl group such as methoxyethyl.

An alkyl group denoted by $R^2$ or $R^3$ in formula I preferably contains up to 6 carbon atoms and may be, for example, a methyl, ethyl, isopropyl or butyl group. These groups may also be substituted.

A halogen atom denoted by $R^4$ in formula I is preferably F, Cl or Br; an alkyl group may be, for example, methyl or ethyl; an alkoxy group may be, for example, methoxy.

An alkyl group denoted by $R^5$ in formula I may be, for example, methyl, ethyl or isopropyl; it may also be substituted, e.g. by halogen or alkoxy, as in methoxymethyl.

An aliphatic group denoted by $R^6$ in formula I may be, for example, methyl, allyl, isoamyl, hexyl, 3-methylbutyl or 2-ethylhexyl. According to the structure shown in formula I, the 1,2,4-triazole ring is attached to the coupling position of the yellow coupler by one of its two adjacent ring nitrogen atoms. Since, however, it has to this day not been fully clarified whether this represents the true structure, formula I should be taken to apply also to isomers in which the 1,2,4-triazole ring may be attached to the coupling position by any of its other ring nitrogen atoms.

Examples of suitable yellow DIR couplers according to the present invention are shown below (iprop denotes isopropyl).

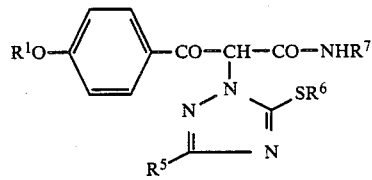

| Compound | $R^1$ | $R^5$ | $R^6$ | $R^7$ |
|---|---|---|---|---|
| 1 | $-C_{16}H_{33}-n$ | H | $-C_6H_{13}-n$ | ![Cl, OCH3, OCH3 phenyl] |
| 2 | $-C_{16}H_{33}-n$ | H | $-C_6H_{13}-n$ | ![OC2H5, OC2H5 phenyl] |
| 3 | $-C_{16}H_{33}-n$ | H | $-C_6H_{13}-n$ | ![Cl, O-iprop, O-iprop phenyl] |
| 4 | $-C_{16}H_{33}-n$ | H | $-C_5H_{11}-n$ | ![Cl, O-iprop, O-iprop phenyl] |
| 5 | $-C_{16}H_{33}-n$ | H | $-CH(CH_3)-CH_2-CH(CH_3)-CH_3$ | ![Cl, O-iprop, O-iprop phenyl] |
| 6 | $-C_{16}H_{33}-n$ | H | $-C_6H_{13}-n$ | ![OCH3, Cl, OCH3 phenyl] |
| 7 | $-C_{16}H_{33}-n$ | H | $-C_6H_{13}-n$ | ![O-iprop, O-iprop phenyl] |

-continued

| Compound | $R^1$ | $R^5$ | $R^6$ | $R^7$ |
|---|---|---|---|---|
| 8 | $-C_{16}H_{33}-n$ | H | $-C_6H_{13}-n$ | 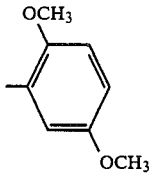 |
| 9 | $CH_3$ | H | $-C_6H_{13}-n$ | 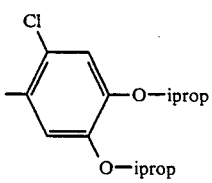 |
| 10 | $-C_{16}H_{33}-n$ | $H_3C-O-CH_2-$ | $-C_6H_{13}-n$ | 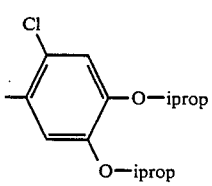 |
| 11 | $-C_2H_4-O-CH_3$ | H | $-C_6H_{13}-n$ | 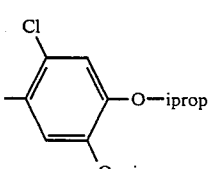 |
| 12 | $-C_{16}H_{33}-n$ | H | $-CH_2-CH_2-CH-CH_3$<br>$\phantom{-CH_2-CH_2-}CH_3$ | 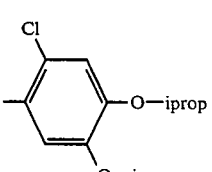 |
| 13 | $-C_{16}H_{33}-n$ | H | $-C_6H_{13}-n$ | 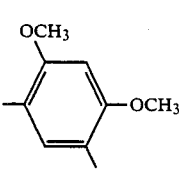 |
| 14 | $-C_{16}H_{33}-n$ | H | $-C_6H_{13}-n$ | 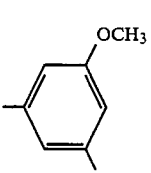 |
| 15 | $-C_{16}H_{33}-n$ | H | $-CH_2-CH-C_4H_9$<br>$\phantom{-CH_2-}C_2H_5$ | 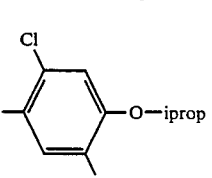 |

The DIR couplers according to the invention corresponding to formula I are readily obtained by the condensation of known α-halogen-benzoyl acetanilides corresponding to formula II

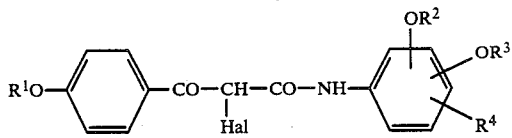

wherein
R¹ to R⁴ have the meanings already indicated and
Hal denotes a halogen atom, in particular chlorine or bromine,
with triazoles corresponding to formula III

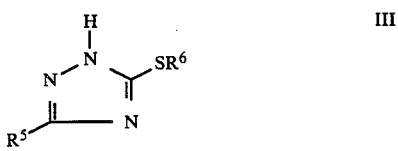

wherein $R^5$ and $R^6$ have the meanings already indicated.

The reaction is advantageously carried out in an organic solvent such as dimethylformamide, acetonitrile or acetone in the presence of a base such as triethylamine or a caustic alkali.

The triazoles corresponding to formula III may in turn be prepared, for example, by reaction of the corresponding 3-mercapto-1,2,4-triazoles with suitable alkyl halides.

Since the triazoles corresponding to formula III may occur in various tautomeric forms and various resonating structures may be assigned to them according to the azeniate ion, condensation could conceivably involve the linkage of any of the ring nitrogen atoms to the carbon atom in the coupling position. This would explain the occurrence of corresponding isomers. This isomerism, however, does not affect the use properties of the DIR couplers according to the invention and a detailed discussion of the structure of the possible isomers is therefore not necessary.

The preparation of DIR couplers according to the invention is explained below with reference to the DIR coupler referred to as compound 3, used as example.

COMPOUND 3

63.6 g of KOH followed by 332 g of α-hexadecyloxy-benzoyl-α,2-dichloro-4,5-diisopropoxy-acetanilide were added with stirring to a solution of 92.5 g of 3-hexylthio-1,2,4-triazole in 1500 ml of acetonitrile. The temperature rose to 50° C. The mixture was stirred for a further 2 hours at this temperature and then cooled. The precipitated product was suction filtered, washed twice with 1000 ml portions of water, taken up in 2000 ml of acetone and precipitated by the addition of 100 ml of concentrated hydrochloric acid and 2000 ml of water. The product, which crystallized when left to stand overnight, was suction filtered and dried. Yield: 303 g, m.pt. 54°-55° C.

The compounds of the present invention are suitable for use as yellow DIR couplers in colour photographic recording materials, in particular in multi-layered materials. As yellow couplers, they are preferably associated with a light sensitive silver halide emulsion layer which has its predominant sensitivity in the blue spectral region of visible light. The special advantage of the yellow DIR coupler according to the invention, namely the comparatively slight inhibition of development in the layer to which such a compound is assigned, combined with comparatively powerful inhibition of development in adjacent layers to which it is not assigned, is, of course, particularly important in a multi-layered colour photographic recording material which in addition to containing a predominantly blue sensitive silver halide emulsion layer contains other light sensitive silver halide emulsion layers which are predominantly sensitive to the green or red spectral region of visible light.

Owing to their very powerful activity, the DIR couplers according to the invention may be used in comparatively small quantities to produce the desired effects, in particular the inter image effect. This enables the DIR couplers according to the invention to be used not only in the blue sensitive layers which produce yellow dye but also in other layers without giving rise to excessive side densities in these layers. The DIR couplers according to the invention may advantageously also be used in magenta layers and in cyan layers. When these yellow couplers are used in such layers they do, of course, slightly increase the unwanted yellow side density of the particular image dye, but this can easily be compensated for by suitable masking methods.

For the preparation of the light sensitive colour photographic recording materials, the diffusion resistant DIR couplers of the present invention may be incorporated in known manner in the casting solution for the silver halide emulsion layers or other colloid layers, optionally together with other couplers. Oil soluble or hydrophobic couplers, for example, may advantageously be added to a hydrophilic colloid solution from a solution in a suitable coupler solvent (oil former), optionally in the presence of a wetting or a dispersing agent. The hydrophilic casting solution may, of course, contain the usual additives in addition to the binder. The coupler solution need not be directly dispersed in the casting solution for the silver halide emulsion layer or other water permeably layer but may advantageously first be dispersed in an aqueous, light insensitive solution of a hydrophilic colloid and the resulting mixture may then be mixed, either directly or optionally after removal of the low boiling organic solvent used, with the casting solution for the light sensitive silver halide emulsion layer or other water permeable layer before the solution is cast.

The light sensitive silver halide emulsions may be emulsions of silver chloride, silver bromide, or mixtures thereof, optionally with a silver iodide content of up to 10 mol %, in one of the commonly used hydrophilic binders. The binder for photographic layers is preferably gelatine although this may be partly or completely replaced by other natural or synthetic binders.

The emulsions may be chemically and spectrally sensitized in the usual manner and the emulsion layers as well as other, light insensitive layers may be hardened with known hardeners in the usual manner.

Colour photographic recording materials normally contain at least one silver halide emulsion layer for the recording of light from each of the three spectral regions, red, green and blue. For this purpose, the light sensitive layers are spectrally sensitized in known manner with suitable sensitizing dyes. Blue sensitive silver halide emulsion layers need not necessarily contain a spectral sensitizer since the intrinsic sensitivity of the silver halide is in many cases sufficient for recording blue light.

Each of the above mentioned light sensitive layers may consist of a single layer or the layers may be combined as two or more silver halide emulsion partial layers in known manner, e.g. as in the so called double layer arrangement (DE-C- No. 1 121 470). Red sensitive silver halide emulsion layers are normally arranged closer to the layers support than green sensitive silver halide emulsion layers which in turn are arranged closer to the support than the blue sensitive layers, and a light insensitive yellow filter layer is generally interposed between the green sensitive layers and the blue sensitive layers, although other arrangements could conceivably be used. A light insensitive inter layer which may contain substances to prevent accidental diffusion of developer oxidation product is generally arranged between layers differing in their spectral sensitivity. If a material contains several silver halide emulsion layers of the same spectral sensitivity, these layers may be directly adjacent to one another or they may be separated by a light sensitive layer having a different spectral sensitivity (DE-A No. 1 958 709, DE-A No. 2 530 645, DE-A No. 2 622 922).

Colour photographic recording materials for the production of multi-colour images normally contain colour producing compounds, in this case in particular colour couplers, in spatial and spectral association with the silver halide emulsion layers of the various spectral sensitivities for the production of partial images in the different colours, cyan, magenta and yellow.

By "spatial association" is meant that the colour coupler is situated in such a spatial relationship to the silver halide emulsion layer that the coupler and the layer can interact so that an image wise correspondence between the silver image produced on development and the colour image produced from the colour coupler can be obtained. This is generally achieved by introducing the colour coupler into the silver halide emulsion layer itself or arranging it in an adjacent layer of binder which may be insensitive to light.

By "spectral association" is meant that the spectral sensitivity of each of the light sensitive silver halide emulsion layers and the colour of the partial colour image produced from the spatially associated colour coupler have a particular relationship to one another, each of the spectral sensitivities (red, green, blue) being associated with a different colour of the partial colour image (e.g. cyan, magenta, yellow).

Each of the silver halide emulsion layers sensitized to different regions of the spectrum may have one or more than one colour coupler associated with it. When a photographic material contains several silver halide emulsion layers having the same spectral sensitivity, then each of these layers may contain a colour coupler and the various colour couplers need not necessarily be identical, provided only that on colour development they give rise to approximately the same colour, normally a colour which is complementary to the colour of the light to which the particular silver halide emulsion layers are predominantly sensitive.

In a preferred embodiment, therefore, red sensitive silver halide emulsion layers have at least one none diffusible colour coupler associated with them for producing the cyan partial colour image, generally a coupler of the phenol or α-naphthol series. Suitable cyan couplers have been described, for example, in EP-A- No. 0 028 080, EP-A No. 0 067 689, EP-A No. 0 175 573 and EP-A No. 0 184 057; green sensitive silver halide emulsion layers have at least one non diffusible colour coupler associated with them for producing the magenta partial colour image, normally a coupler of the 5-pyrazolone, indazolone or pyrazoloazole series; and blue sensitive silver halide emulsion layers have at least one non diffusible colour coupler associated with them for producing the yellow partial colour image, generally a colour coupler containing an open chain ketomethylene group. Many colour couplers of this kind are known and have been described in numerous patent specifications; see also, for example, the publication "Farbkuppler" by W. Pelz in "Mitteilungen aus den Forschungslaboratorien der Agfa, Leverkusen/München", volume III, page 111 (1961) and the publication by K. Venkataraman in "The Chemistry of Synthetic Dyes", volume 4, 341 to 387, Academic Press (1971).

The colour coupler may be either conventional 4-equivalent couplers or 2-equivalent couplers which require a smaller quantity of silver halide for producing the colour. 2-equivalent couplers are derived, as is known, from 4equivalent couplers in that they carry in their coupling position a substituent which is split off in the coupling reaction. The 2-equivalent couplers include those which are virtually colourless and those which have a intense colour of their own which disappears in the colour coupling reaction to be replaced by the colour of the resulting image dye. The latter couplers may also be present in light sensitive silver halide emulsion layers to serve as masking couplers to compensate for unwanted side densities of the image dyes. 2-equivalent couplers also include the known white couplers which do not give rise to a dye in their reaction with colour developer oxidation products, and the known DIR couplers which carry, in their coupling position, a releasable group which is released as a diffusible development inhibitor in the reaction with colour developer oxidation products. In the process of development, such couplers may also release other photographically active compounds, such as development accelerators or fogging agents.

According to this invention, the colour photographic recording material contains in addition at least one 2-equivalent yellow coupler corresponding to formula I, which coupler may be present not only in the yellow layer but also in the magenta layer and/or in the cyan layer.

In addition to the components already mentioned, the colour photographic recording material according to the present invention may contain other substances as additives, e.g. anti-oxidants,dye stabilizers and agents for influencing the mechanical and electrostatic properties. It is also advantageous to use UV absorbent compounds in one or more of the layers of the recording material, preferably in one of the upper layers, for the purpose of preventing or reducing the deleterious effect of UV light on the colour images produced with the colour photographic recording material of this invention. Suitable UV absorbents have been described, for example, in U.S. Pat. No. 3,253,921, DE-C- No. 2 036 719 and EP-A No. 0 057 160.

The usual layer supports may be used for the materials according to the invention; see Research Disclosure Number 17 643, Section XVII.

The usual hydrophilic film formers may be used as protective colloids or binders for the layers of the recording material, e.g. proteins, in particular gelatine. Casting auxiliaries and softners may also be used; see the compounds mentioned in the aforesaid Research Disclosure Number 17 643, Section IX, XI and XII.

The layers of the photographic material may be hardened in the usual manner, for example with hardeners of the epoxide series, the heterocyclic ethylene imine series and the acryloyl series. Hardening of the layers may also be carried out by the process according to German Offenlegungsschrift No. 2 218 009 to produce colour photographic materials which are suitable for high temperature processing. The photographic layers may also be hardened with hardeners of the diazine, triazine or 1,2-dihydroquinoline series or with vinyl sulphone type hardeners. Other suitable hardeners have been disclosed in German Offenlegungsschriften Nos. 2 439 551, 2 225 230 and 2 317 672 and in the above mentioned Research Disclosure 17 643, Section XI.

Other suitable additives are mentioned in Research Disclosure 17 643 and in "Product Licensing Index" of December 1971, pages 107–110.

The colour photographic images are produced by developing the colour photographic recording material according to the invention with a colour developer compound. Any developer compounds which in the form of their oxidation products are capable of reacting with colour couplers to form azomethine dyes may be used as colour developers. Suitable colour developer compounds include aromatic compounds of the p-phenylendiamine series e.g.N,N-dialkyl-p-phenylene diamines such as N,N-diethyl-p-phenylendiamine, 1-(N-ethyl-N-methyl-sulphonamidoethyl)-3-methyl-p-phenylendiamine, 1-(N-ethyl-N-hydroxyethyl)-3-methyl-p-phenylendiamine and 1-(N-ethyl-N-methoxyethyl)-3-methyl-p-phenylendiamine.

Other suitable colour developers have been described, for example, in J. American Chem. Soc. 73,3100 (1951) and in G. Haist, Modern Photographic Processing, 1979, John Wiley and Sons, New York, pages 545 et seq.

The material is normally bleached and fixed after colour development. Bleaching and fixing may be carried out separately or together. The usual bleaching compounds may be used, e.g. $Fe^{3+}$ salts and $Fe^{3+}$ complex salts such as ferricyanides, dichromates, water soluble cobalt complexes, etc.. Iron-III complexes of aminopolycarboxylic acids are particularly preferred, e.g. the complexes of ethylendiamino-tetracetic acid, of N-hydroxyethyl-ethylene-diamino-triacetic acid and of alkyliminodicarboxylic acids as well as of the corresponding phosphonic acids. Persulphates are also suitable bleaching agents.

EXAMPLE 1

Various colour photographic materials were prepared, each containing a silver halide emulsion layer containing a DIR coupler (donor layer) an interlayer and a silver halide emulsion layer free from DIR coupler (acceptor layer).

The quantities given are based on 1 m². The quantities of silver halide applied are given in terms of the corresponding quantities of $AgNO_3$. The silver halide emulsions were stabilized with 0.5 g of 4-hydroxy-6-methyl-1,3,3a,7-tetraazaindene per 100g of $AgNO_3$.

The following layers were applied in the sequence given to a transparent layer support of cellulose triacetate.

Layer 1: Green sensitized silver iodo bromide emulsion (7 mol % iodide; average grain diameter 0.6 μm) obtained from 4.25 g of $AgNO_3$ with 0.7 g of coupler C-1 and 2.5 g of gelatine Layer 2: (inter layer) obtained from 2.06 g of gelatine and 0.31 g of white coupler W-1

Layer 3: Red sensitized silver iodo bromide emulsion (7 mol % iodide; average grain diameter 0.6 μm) obtained from 4.25 g of $AgNO_3$ with 1 g of coupler M-1, 0.43 m mol of DIR coupler (see Table 1) and 2.5 g of gelatine.

Layer 4: (Protective layer) 0.46 g of gelatine and 0.47 g of carbamoylpyridinium salt (CAS Reg. No. 65411-60-1)

Compounds C-1, M-1 and the DIR couplers were introduced in the form of emulsions as described in Example 2. Different materials 1-7 were obtained by this method, the materials differing only in the DIR coupler used in layer 3. Development was carried out after exposure to reflected light through a grey wedge as described in "The Journal of Photography", 1974, pages 597 and 598.

The results are shown in Table 1. Inhibition is calculated according to the following equation:

$$I = 1 - \frac{\gamma \text{ with DIR coupler}}{\gamma \text{ without DIR coupler}}$$

as described in EP-A- No. 0 145 460.

KE is the difference between the micro density and macro density at macro density=1 as described by James in The Theory of the Photographic Process, 5th Edition, Macmillan Publishing Co. Inc. 1977, page 611.

TABLE 1

| Material | DIR Coupler | Inhibition Layer 1 | Inhibition Layer 3 | KE |
|---|---|---|---|---|
| 1 | — | — | — | 0.11 |
| 2 | A | 46 | 50 | 0.35 |
| 3 | B | 60 | 66 | 0.46 |
| 4 | 9 | 65 | 69 | 0.52 |
| 5 | 7 | 60 | 68 | 0.55 |
| 6 | 3 | 84 | 70 | 0.71 |
| 7 | 12 | 38 | 45 | 0.55 |

The following DIR couplers were used for comparison in materials 2 and 3:

DIR coupler A (compound 4 of DE-A No. 34 27 235):

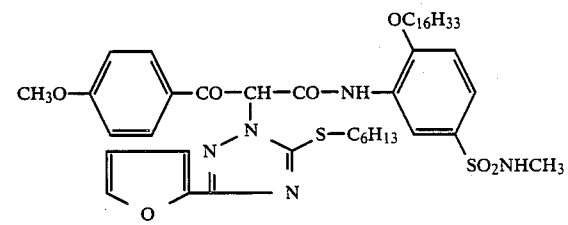

DIR coupler B (compound 202 of DE-A No. 28 42 063)

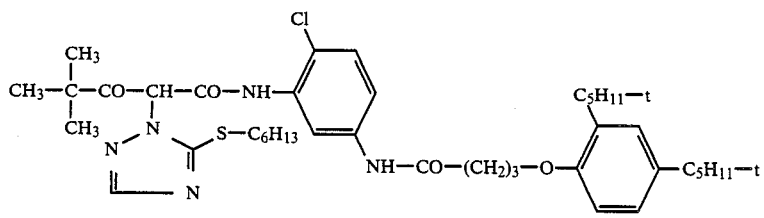

EXAMPLE 2

A colour photographic recording material for colour negative development was prepared by applying the following layers in the given sequence to a transparent layer support of cellulose triacetate. The quantities are based on 1 m². The quantities of silver halide applied are given in terms of the corresponding quantities of AgNO₃. All silver halide emulsion layers were stabilized with 0.5 g of 4-hydroxy-6-methyl-1,3,3a,7-tetraazaindene per 100 g of AgNO³.

Layer 1: (Antihalation layer) black collidal silver sol containing 0.4 g of Ag and 3 g of gelatine Layer 2: (First red sensitized layer) Red sensitized silver iodo bromide emulsion (7 mol % iodide; average grain diameter 0.6 μm) of 2.7 g of AgNO₃ with 0.51 g of coupler C-1, 0.078 g of masking coupler MC-1, $6.6\times 10^{-5}$ mol of DIR coupler (see Table 2) and 1.5 g of gelatine Layer 3: (Second red sensitized layer) red sensitized silver iodo bromide emulsion (10 mol % iodide; average grain diameter 1.5 μm) of 3.8 g of AgNO₃ with 0.137 g of coupler C-1 and 2.7 g of gelatine Layer 4: (Inter layer) 0.15 g of white coupler W-1 and 0.8 g of gelatine Layer 5: (First green sensitized layer) green sensitized silver iodo bromide emulsion (7 mol % iodide; average grain diameter 0.6 μm) of 2.0 g of AgNO₃ with 0.403 g of coupler M-1, 0.175 g of masking coupler MC-2, $4.9\times 10^{-5}$ mol of DIR coupler (see Table 2) and 1.4 g of gelatine Layer 6: (Second green sensitized layer) green senstized silver iodo bromide emulsion (4 mol % iodide; average grain diameter 1.4 μm) of 2.5 g of AgNO₃ with 0.2 g of coupler M-1 and 1.6 g of gelatine Layer 7: (Inter layer) 0.1 g of white coupler W-1 and 0.34 g of gelatine Layer 8: (Yellow filter layer) Yellow colloidal silver containing 71 mg of Ag, 0.1 g of white coupler W-1 and 0.5 g of gelatine Layer 9: (First blue sensitive layer) silver iodo bromide emulsion (4.5 mol % iodide; average grain diameter 0.5 μm) of 0.5 g of AgNO₃ with 0.8 g of coupler Y-1, $3.7\times 10^{-5}$ mol of DIR coupler (see Table 2) and 1.4g of gelatine Layer 10: (Second blue sensitive layer) Silver iodo bromide emulsion (10 mol % iodide; average grain diameter 1.5 μm) of 0.8 g of AgNO₃ with 2.81 g of coupler Y-1 and 1.4 g of gelatine Layer 11: (Protective layer) 0.7 g of gelatine Layer 12: (Hardening layer) 0;24 g of gelatine and 0.7 g of carbamoyl pyridinium salt (CA Reg. No. 65411-60-1).

Compounds C-1, M-1, MC-2, and Y-1 and the DIR couplers were used in the form of emulsions containing 1 part of gelatine, 2 parts of tricresylphosphate in the case of coupounds M-1 and MC-2 and of di-n-butylphthalate in all other cases, and 0.1 part of the sodium salt of triisopropylnaphthalene sulphonic acid as wetting agent, based in each case on 1 part of the compound used.

Various versions (materials 8–13) of the recording material composed of the layers described above were prepared. These versions differed from one another only in the DIR couplers used in layers 2, 5 and 9.

The results obtained after processing as described in Example 1 are shown in Table 2. The inter image effects IIE are calculated as follows:

$$IIE_{cyan} = \frac{red - \gamma w}{\gamma w} \ ; \ IIE_{magenta} = \frac{green - \gamma w}{\gamma w}$$

In these equations,

γred: denotes gradation on selective exposure to red light

γgreen: denotes gradation on selective exposure to green light

γw: denotes gradation on exposure to white light $KE_{cyan}$: denotes DE in the red sensitized layer $KE_{magenta}$: denotes DE in the green sensitized layer

TABLE 2

| Material | DIR Coupler | $IIE_{cyan}$ | $IIE_{magenta}$ | $KE_{cyan}$ | $KE_{magenta}$ |
|---|---|---|---|---|---|
| 8 | A | 26 | 34 | 0.22 | 0.30 |
| 9 | B | 24 | 37 | 0.23 | 0.27 |
| 10 | C | 30 | 38 | 0.23 | 0.29 |
| 11 | 3 | 44 | 71 | 0.40 | 0.40 |
| 12 | 12 | 42 | 64 | 0.37 | 0.40 |
| 13 | 6 | 38 | 45 | 0.34 | 0.31 |

DIR coupler C used for comparison in material 10 corresponds to the following formula:

DIR Coupler C (prepared from coupler No. 18 of DE-A No. 28 42 063):

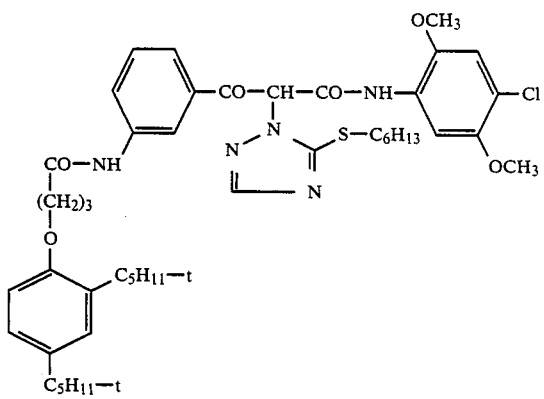

EXAMPLE 3

A colour photographic recording material for colour negative development was prepared as in Example 2 but with the following layers:

Layer 1: (Antihalation layer) black colloidal silver sol containing 0.33 g of Ag and 2.0 g of gelatine Layer 2: (Inter layer) 0.5 g of gelatine Layer 3: (First red sensitized layer) red sensitized silver iodobromide emulsion (6 mol % iodide; average grain diameter 1.0 μm) obtained from 3.5 g of $AgNO_3$ with 1 g of coupler C-1, 50 mg of compound MC-1 and 2.5 g of gelatine Layer 4: (Second red sensitized layer) red sensitized silver iodobromide emulsion (8 mol % iodide; average grain diameter 1.6 μm) obtained from 4.0 g of $AgNO_3$ with 0.3 g of coupler C-1, 3 mg of compound MC-1 and 4 g of gelatine Layer 5: (Inter layer) 1.2 g of gelatine Layer 6: (First green sensitized layer) green sensitized silver iodobromide emulsion (6 mol % iodide; average grain diameter 1.0 μm) obtained from 1.5 g of $AgNO_3$ with 0.5 g of coupler M-1, 60 mg of compound MC-2 and 1.4 g of gelatine Layer 7: (Second green sensitized layer) green sensitized silver iodobromide emulsion (8 mol % iodide; average grain diameter 1.6 μm) obtained from 2.5 g of $AgNO_3$ with 0.4 g of coupler M-1, 35 mg of compound MC-2 and 2 g of gelatine Layer 8: (Yellow filter layer) yellow colloidal silver sol containing 0.05 g of Ag and 0.2 g of gelatine Layer 9: (First blue sensitive layer) silver iodobromide emulsion (6 mol % iodide; average grain diameter 1.0 μm) obtained from 1.0 g of $AgNO_3$ with 0.7 g of coupler Y-1 and 1.2 g of gelatine Layer 10: (Second blue sensitive layer) silver iodobromide emulsion (8 mol % iodide; average grain diameter 1.6 μm) obtained from 1.2 g of $AgNO_3$, 0.4 g of coupler Y-1 and 0.8 g of gelatine Layer 11: (Protective layer) 1.5 g of gelatine Layer 12: (Hardening layer) same as Layer 12 of Example 2.

Two different versions of the recording material composed as described above were prepared. These versions differed only in the nature and quantity of the additional DIR coupler introduced into layers 3, 6 and 9 (materials 14 and 15).

MATERIAL 14

DIR coupler 3 was added to layers 3, 6 and 9 in the following quantities per $m^2$:

Layer 3: 0.03 g
Layer 6: 0.01 g
Layer 9: 0.05 g.

MATERIAL 15

Same as material 14 except that DIR coupler A was added to layer 9 in a quantity of 0.13 g/$m^2$ instead of DIR coupler 3.

The results obtained after processing as described in Example 1 are summarized in Table 3.

TABLE 3

|  | $IIE_{cyan}$ | $IIE_{magenta}$ | $KE_{cyan}$ | $KE_{magenta}$ |
|---|---|---|---|---|
| Material 14 | 37 | 50 | 0.26 | 0.34 |
| Material 15 | 37 | 79 | 0.41 | 0.35 |

The advantages of material 15 compared with material 14 are seen in the enhanced inter image effect and greater edge effect, with the result that improved colour separation and improved sharpness are obtained.

The increased quantity of DIR coupler in material 15 is no disadvantage for the partial colour yellow produced and does not interfere with the development of other film materials (due to alteration in the sensitometric properties such as gradation and sensitivity) if any commercially available colour negative material is developed in the same developer after it has been used for developing a large quantity of material 15.

The following compounds were used in Examples 1, 2 and 3:

Coupler C-1

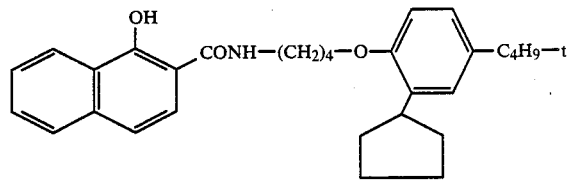

White coupler W-1

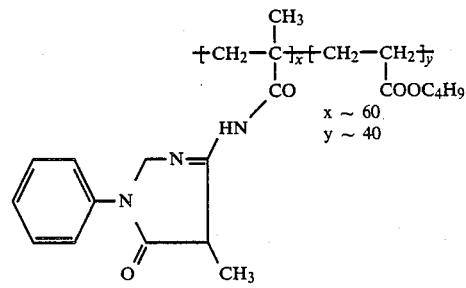

Coupler M-1

-continued

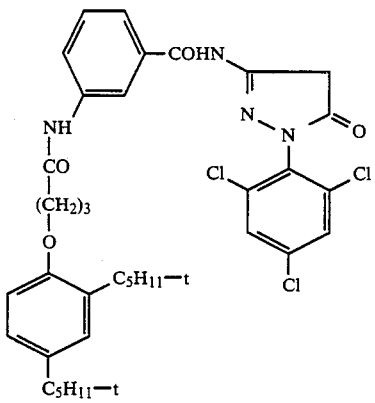

Masking coupler MC-1

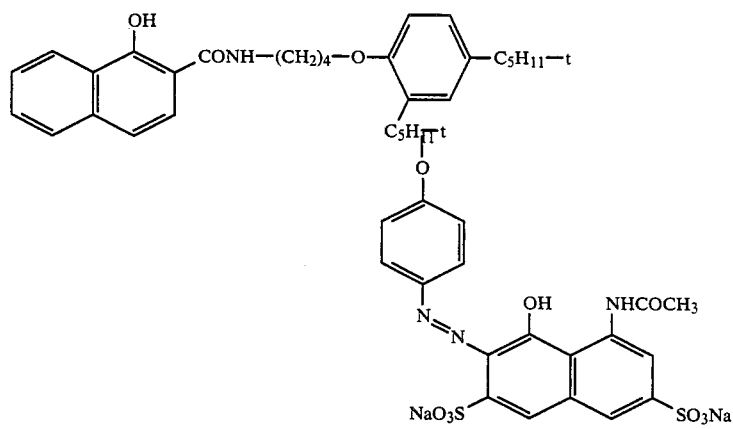

Masking coupler MC-2

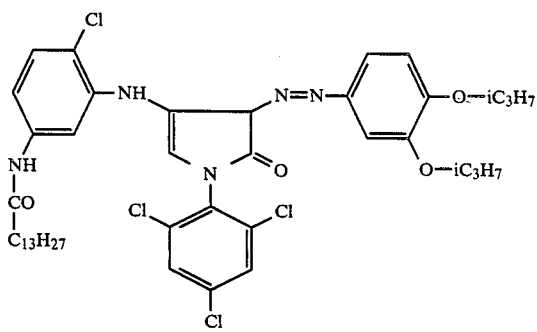

Coupler Y-1

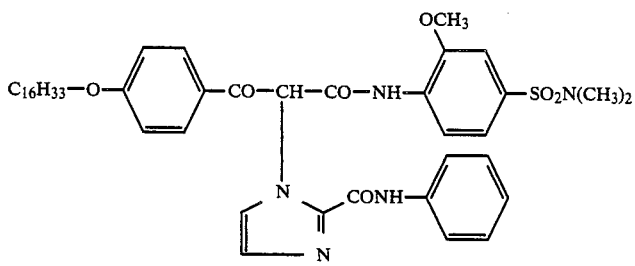

We claim:

1. Colour photographic recording material having at least one predominantly blue sensitive silver halide emulsion layer unit associated with at least one yellow coupler, a predominantly green sensitive silver halide emulsion layer unit associated with at least one magenta coupler and a predominantly red sensitive silver halide emulsion layer unit associated with at least one cyan coupler, each of said silver halide emulsion layer units comprising two or more silver halide partial layers, characterised in that at least one partial layer of the predominantly green sensitive silver halide emulsion layer unit or of the predominantly red sensitive silver halide emulsion layer unit contains a compound corresponding to the following formula:

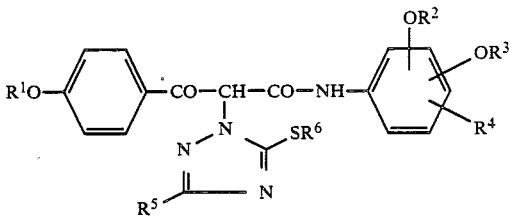

wherein
$R^1$ denotes a straight chained or branched alkyl group with up to 18 carbon atoms;
$R^2$, $R^3$ denote identical or different alkyl groups with up to 18 carbon atoms;
$R^4$ denotes Cl;
$R^5$ denotes H or alkyl with up to 9 carbon atoms;
$R^6$ denotes a saturated or unsaturated aliphatic group with up to 10 carbon atoms
and the total number of carbon atoms in $R^5$ and $R^6$ is not less than 5 and not greater than 10.

2. Colour photographic recording material according to claim 1, characterised in that the DIR coupler is contained in a predominantly red sensitive silver halide emulsion layer.

* * * * *